United States Patent
Hasse et al.

(10) Patent No.: US 10,472,324 B2
(45) Date of Patent: Nov. 12, 2019

(54) 2-CYANO-3-CYCLOPROPYL-3-HYDROXY-N-ARYL-THIOACRYLAMIDE DERIVATIVES

(71) Applicant: Algiax Pharmaceuticals GmbH, Erkrath (DE)

(72) Inventors: Birgit Hasse, Wuppertal (DE); Guido Koopmans, Sittard (NL)

(73) Assignee: ALGIAX PHARMACEUTICALS GMBH, Erkath (DE)

( * ) Notice: Subject to any disclaimer, the term of this patent is extended or adjusted under 35 U.S.C. 154(b) by 0 days.

(21) Appl. No.: 15/126,378

(22) PCT Filed: Mar. 15, 2015

(86) PCT No.: PCT/EP2015/055379
§ 371 (c)(1),
(2) Date: Sep. 15, 2016

(87) PCT Pub. No.: WO2015/140081
PCT Pub. Date: Sep. 24, 2015

(65) Prior Publication Data
US 2017/0088513 A1    Mar. 30, 2017

Related U.S. Application Data

(60) Provisional application No. 61/954,844, filed on Mar. 18, 2014.

(30) Foreign Application Priority Data

Mar. 18, 2014 (EP) ..................................... 14000994

(51) Int. Cl.
C07C 327/44 (2006.01)

(52) U.S. Cl.
CPC ........ *C07C 327/44* (2013.01); *C07C 2601/02* (2017.05)

(58) Field of Classification Search
CPC .......................... C07C 327/44; C07C 2101/02
See application file for complete search history.

(56) References Cited

U.S. PATENT DOCUMENTS

| | | | |
|---|---|---|---|
| 3,536,809 A | 10/1970 | Applezweig | |
| 3,598,123 A | 8/1971 | Zaffaroni | |
| 3,845,770 A | 11/1974 | Theeuwes | |
| 3,916,899 A | 11/1975 | Theeuwes | |
| 4,008,719 A | 2/1977 | Theeuwes | |
| 5,059,595 A | 10/1991 | Le Grazie | |
| 5,073,543 A | 12/1991 | Marshall et al. | |
| 5,120,548 A | 6/1992 | Mclelland | |
| 5,134,127 A | 7/1992 | Stella | |
| 5,354,556 A | 10/1994 | Sparks | |
| 5,591,767 A | 1/1997 | Mohr et al. | |
| 5,639,476 A | 6/1997 | Oshlack et al. | |
| 5,674,533 A | 10/1997 | Santus et al. | |
| 5,733,566 A | 3/1998 | Lewis | |
| 5,760,066 A * | 6/1998 | Tang ..................... | C07C 327/44 514/378 |
| 2003/0229134 A1 | 12/2003 | Filbin | |

FOREIGN PATENT DOCUMENTS

| | | |
|---|---|---|
| EP | 731099 B1 | 6/2000 |
| EP | 1500643 A1 | 1/2005 |
| WO | 2000069842 A1 | 11/2000 |

(Continued)

OTHER PUBLICATIONS

PCT/EP2015/055379 International Search Report dated Jun. 16, 2015.
Chaplan et al. "Quantitative Assessment of Tactile Allodynia in the Rat Paw." Journal of Neuroscience Methods, 1994, 53:55-63, Elsevier Science B.V.
Chung et al. "Segmental Spinal Nerve Ligation Model of Neuropathic Pain." Methods in Molecular Medicine, 2004, vol. 99: Pain Research: Methods and Protocols, Humana Press Inc., Totowa, NJ.
Lewin et al. "meta- and para-Isothiocyanato-t-butylbicycloorthobenzoate: Irreversible Ligands of the y-Aminobutyric Acid Regulated Chloride Ionophore." Molecular Pharmacology, 1989, 35:189-194, The Americvan Society of Pharmacology and Experimental Therapeutics.
Mohler et al. "Heterogeneity of GABA—Receptors: Cell-Specific Expression, Pharmacology, and Regulation." Neurochemical Research, 1995, 20(5)631-636, Plemu, Publishing Corporation.

(Continued)

*Primary Examiner* — Sudhakar Katakam
(74) *Attorney, Agent, or Firm* — Ballard Spahr LLP

(57) ABSTRACT

A compound of the formula (I) or a tautomeric isoform thereof wherein R1 is selected from the group consisting of halogen, nitro, lower alkyl sulfonyl, cyano, trifluromethyl lower alkyl, lower alkoxy, lower alkoxycarbonyl, carboxy, lower alkyl aminosulfonyl, perfluoro lower alkyl, lower alkylthio, hydroxy lower alkyl, alkoxy lower alkyl, lower alkylthio lower alkyl, lower alkylsulfinyl lower alkyl, lower alkylsulfonyl lower alkyl, lower alkylsulfonyl, lower alkanoyl, aroyl, aryl, aryloxy and R2 is selected from the group consisting of hydrogen, alkyl, alkoxy, alkylthio, and alkylcarbonyl, and their non-toxic, pharmaceutically acceptable base addition salts or pro-drugs thereof. The compounds of the invention are useful in the treatment of nervous system diseases and disorders, which are responsive to modulation of the $GABA_A$ receptor complex.

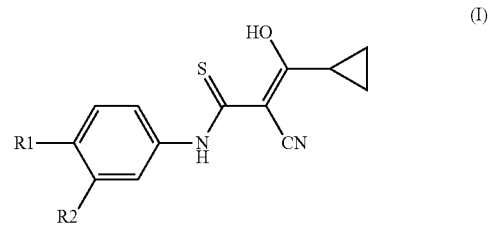

(I)

13 Claims, 2 Drawing Sheets

(56) References Cited

FOREIGN PATENT DOCUMENTS

WO    2006020358 A2    2/2006
WO    2014/001281 A1    1/2014

OTHER PUBLICATIONS

Pritchett et al. "Type I and Type II GABBAA-Benzodiazepine Receptors Produced in Transfected Cells." Science, Sep. 22, 1989, 245(4924)1389-1392; American Association for the Advancement of Science, New York.
Knight et al. "Molecular Size of Recombinant Alpha1Beta1 and Alpha1BetaGamma2 GABAA Receptors Expressed in Sf9 Cells." Receptors and Channels, 1998, 6:1-18, Overseas Publishers Association.
Burger et al. "The Significance of Drug Metabolism in Medicinal Chemistry." 1995 p. 172-178, Manfred E Wolff Ed 5th Ed.
Balant and Doelker, "Metabolic Considerations in Prodrug Design." 1995, p. 949-982, Manfred E Wolff Ed 5th Ed 5th Ed.
Wilen et al. "Tetrahedron Report No. 38: Strategies in Optical Resolutions." Tetrahedron, 1977, 33:2725-2736, Pergamon Press, Great Britain.
Wilen, "Table 13: Resolutions of Amino Acids, Amino Acid Derivatives and Related Compounds." Tables of Resolving Agents and Optical Resolutions, 1972, p. 268, E.L. Eliel, Ed., Univ of Notre Dame Press, Notre Dame, IN.
Carstensen, "Drug Stability: Principles & Practice," 1995, 2d Ed. Marcel Dekker, NY, pp. 379-380.

* cited by examiner

A)

B)

A)

B)

2-CYANO-3-CYCLOPROPYL-3-HYDROXY-N-ARYL-THIOACRYLAMIDE DERIVATIVES

TECHNICAL FIELD

The invention relates to compounds of formula I or a tautomeric isoform and their non-toxic, pharmaceutically acceptable salts, pharmaceutical compositions containing these compounds, a process for their preparation and their use in the modulation of the $GABA_A$ receptor complex.

SUMMARY OF THE INVENTION

In one aspect of the invention a compound is provided according to formula I or a tautomeric isoform thereof,

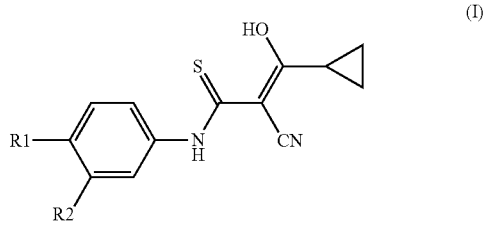

(I)

wherein R1 is selected from the group consisting of halogen, nitro, lower alkyl sulfonyl, cyano, trifluromethyl lower alkyl, lower alkoxy, lower alkoxycarbonyl, carboxy, lower alkyl aminosulfonyl, perfluoro lower alkyl, lower alkylthio, hydroxy lower alkyl, alkoxy lower alkyl, lower alkylthio lower alkyl, lower alkylsulfinyl lower alkyl, lower alkylsulfonyl lower alkyl, lower alkylsulfinyl, lower alkanoyl, aroyl, aryl, aryloxy and R2 is selected from the group consisting of hydrogen, alkyl, alkoxy, alkylthio, and alkylcarbonyl and their non-toxic, pharmaceutically acceptable base addition salts or pro-drugs thereof.

In some embodiments, RI is selected from a group consisting of fluorine, chlorine, jodine, trifluoromethyl, cyano, nitro, methansulfinyl, methansulfonyl, trifluoromethansulfinyl and trifluoromethansulfonyl, and R2 is hydrogen, ethyl or methyl.

In some embodiments, the compound is selected from the group consisting of 2-cyano-3-cyclopropyl-3-hydroxy-N-(3-methyl-4-trifluormethyl-phenyl)-thioacrylamide, 2-cyano-3-cyclopropyl-3-hydroxy-N-(3-ethyl-4-trifluormethyl-phenyl)-thioacrylamide, 2-cyano-3-cyclopropyl-N-(4-fluoro-3-methyl-phenyl)-3-hydroxy-thioacrylamide, 2-cyano-3-cyclopropyl-N-(4-fluoro-3-ethyl-phenyl)-3-hydroxy-thioacrylamide, 2-cyano-3-cyclopropyl-N-(4-fluoro-phenyl)-3-hydroxy-thioacrylamide 2-cyano-3-cyclopropyl-3-hydroxy-N-(3-methyl-4 -nitro-phenyl)-thioacrylamide, 2-cyano-3-cyclopropyl-3-hydroxy-N-(3-ethyl-4 -nitro-phenyl)-thioacrylamide, 2-cyano-3-cyclopropyl-3-hydroxy-N-(4-nitro-phenyl)-thioacrylamide, 2-cyano-3-cyclopropyl-3-hydroxy-N-(4-trifluoromethanesulfinyl-phenyl)-thioacrylamide, 2-cyano-N-(4 -cyano-3-methyl-phenyl)-3-cyclopropyl-3-hydroxy-thioacrylamide, 2-cyano-N-(4-cyano-3-ethyl-phenyl)-3-cyclopropyl-3-hydroxy-thioacrylamide, 2-cyano-N-(4-cyano-phenyl)-3-cyclopropyl-3-hydroxy-thioacrylamide, 2-cyano-3-cyclopropyl-3-hydroxy-N-(4-trifluoromethanesulfinyl-3-methyl-phenyl)-thioacrylamide, 2-cyano-3-cyclopropyl-3-hydroxy-N-(4 -trifluoro-methanesulfonyl-phenyl)-thioacrylamide, 2-cyano-3-cyclopropyl-3-hydroxy-N-(4-trifluoromethanesulfonyl-3-methyl-phenyl)-thioacrylamide, 2-cyano-3-cyclopropyl-3-hydroxy-N-(4-((trifluoromethyl)thio)phenyl)-thioacrylamide, 2-cyano-3-cyclopropyl-3-hydroxy-N-(3-methyl-4-((trifluoromethyl)thio)phenyl)-thioacrylamide, 2-cyano-3-cyclopropyl-N-(4-chloro-3-methyl-phenyl)-3-hydroxy-thioacrylamide, 2-cyano-3-cyclopropyl-N-(4-chloro-3-ethyl-phenyl)-3-hydroxy-thioacrylamide, 2-cyano-3-cyclopropyl-N-(4-chloro-phenyl)-3-hydroxy-thioacrylamide and their tautomeric isoforms, non-toxic, pharmaceutically acceptable salts or pro-drugs thereof.

In a related aspect, a pharmaceutical composition is provided, which includes a therapeutically effective amount of at least one compound according to formula (I), or an tautomer thereof, or any of its isomers or any mixture of its isomers, or a pharmaceutically acceptable salt thereof, optionally together with at least one acceptable and inert pharmaceutical carrier, excipient or diluent.

In some embodiments, R1 is individually selected from the group consisting of fluorine, chlorine, jodine, trifluoromethyl, cyano, nitro, methansulfinyl, methansulfonyl, trifluoromethansulfinyl and trifluoromethansulfonyl, and R2 is hydrogen. In further embodiments, R1 is individually selected from the group consisting of fluorine, chlorine, jodine, trifluoromethyl, cyano, nitro, methansulfinyl, methansulfonyl, trifluoromethansulfinyl and trifluoromethansulfonyl, and R2 is methyl or ethyl.

In some embodiments, the active compound is selected from the group consisting of 2-cyano-3-cyclopropyl-3-hydroxy-N-(3-methyl-4-trifluormethyl-phenyl)-thioacrylamide, 2-cyano-3-cyclopropyl-3-hydroxy-N-(3-ethyl-4-trifluormethyl-phenyl)-thioacrylamide, 2-cyano-3-cyclopropyl-N-(4-fluoro-3-methyl-phenyl)-3-hydroxy-thioacrylamide, 2-cyano-3-cyclopropyl-N-(4-fluoro-3-ethyl-phenyl)-3-hydroxy-thioacrylamide, 2-cyano-3-cyclopropyl-N-(4-fluoro-phenyl)-3-hydroxy-thioacrylamide 2-cyano-3-cyclopropyl-3-hydroxy-N-(3-methyl-4nitro-phenyl)-thioacrylamide, 2-cyano-3-cyclopropyl-3-hydroxy-N-(3-ethyl-4-nitro-phenyl)-thioacrylamide, 2-cyano-3-cyclopropyl-3-hydroxy-N-(4-nitro-phenyl)-thioacrylamide, 2-cyano-3-cyclopropyl-3-hydroxy-N-(4-trifluoromethanesulfinyl-phenyl)-thioacrylamide, 2-cyano-N-(4-cyano-3-methyl-phenyl)-3-cyclopropyl-3-hydroxy-thioacrylamide, 2-cyano-N-(4-cyano-3-ethyl-phenyl)-3-cyclopropyl-3-hydroxy-thioacrylamide, 2-cyano-N-(4-cyano-phenyl)-3-cyclopropyl-3-hydroxy-thioacrylamide, 2-cyano-3-cyclopropyl-3-hydroxy-N-(4-trifluoromethanesulfinyl-3-methyl-phenyl)-thioacrylamide, 2-cyano-3-cyclopropyl-3-hydroxy-N-(4-trifluoro-methanesulfonyl-phenyl)-thioacrylamide, 2-cyano-3-cyclopropyl-3-hydroxy-N-(4-trifluoromethanesulfonyl-3-methyl-phenyl)-thioacrylamide, 2-cyano-3-cyclopropyl-3-hydroxy-N-(4-((trifluoromethyl)thio)phenyl)-thioacrylamide, 2-cyano-3-cyclopropyl-3-hydroxy-N-(3-methyl-4-((trifluoromethyl)thio)phenyl)-thioacrylamide, 2-cyano-3-cyclopropyl-N-(4-chloro-3-methyl-phenyl)-3-hydroxy-thioacrylamide, 2-cyano-3-cyclopropyl-N-(4-chloro-3-ethyl-phenyl)-3-hydroxy-thioacrylamide, 2-cyano-3-cyclopropyl-N-(4-chloro-phenyl)-3-hydroxy-thioacrylamide and their tautomeric isoforms, non-toxic, pharmaceutically acceptable base addition salts or pro-drugs thereof.

In a related aspect the compound or composition is a medicine. In some embodiments, medicine is for use in the treatment, prevention or alleviation of a disease or a disorder or a condition of a living animal body, including a human, which disorder, disease or condition is responsive to modulation of the $GABA_A$ receptor complex.

In a related aspect, a process for preparing the compound of formula I is provided, which includes reacting a compound of formula II

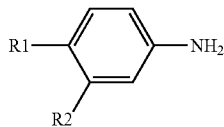

with thiophosgen to form a compound of formula III

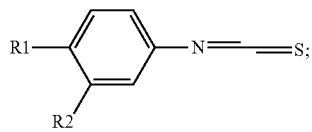

and reacting formula (III) with 3-cyclopropyl-3-oxopropionitril to obtain the compound of formula I;
wherein R1 is selected from the group consisting of halogen, nitro, lower alkyl sulfonyl, cyano, trifluromethyl lower alkyl, lower alkoxy, lower alkoxycarbonyl, carboxy, lower alkyl aminosulfonyl, perfluoro lower alkyl, lower alkylthio, hydroxy lower alkyl, alkoxy lower alkyl, lower alkylthio lower alkyl, lower alkylsulfinyl lower alkyl, lower alkylsulfonyl lower alkyl, lower alkylsulfinyl, lower alkanoyl, aroyl, aryl, aryloxy and R2 is selected from the group consisting of hydrogen, alkyl, alkoxy, alkylthio, and alkylcarbonyl and their non-toxic, pharmaceutically acceptable base addition salts or pro-drugs thereof.

BRIEF DESCRIPTION OF THE DRAWINGS

FIG. 1 (B) shows the 50% paw withdrawal threshold (g) after spinal nerve ligation (Chung model) and oral gavage of 10 mg/kg of Example 3 (2-Cyano-3-cyclopropyl-3-hydroxy-N-(3-methyl-4-nitro-phenyl)-thioacrylamide), Example 4 (2-Cyano-3-cyclopropyl-3-hydroxy-N-(4-nitro-phenyl)-thioacrylamide), Example 6 (2-Cyano-N-(4-cyano-3-methyl-phenyl)-3-cyclopropyl-3-hydroxy-thioacrylamide) or vehicle from DPO 14 till DPO 19. *** p<0.001

FIG. 2 (B) shows the 50% paw withdrawal threshold (g) after capsaicin induced pain and oral gavage of 10 mg/kg of Example 2 (2-Cyano-3-cyclopropyl-N-(4-fluoro-3-methyl-phenyl)-3-hydroxy-thioacrylamide), Example 6 (2-Cyano-N-(4-cyano-3-methyl-phenyl)-3-cyclopropyl-3-hydroxy-thioacrylamide) or vehicle about 40 minutes after capsaicin injection. * p<0.05

Figure 1:
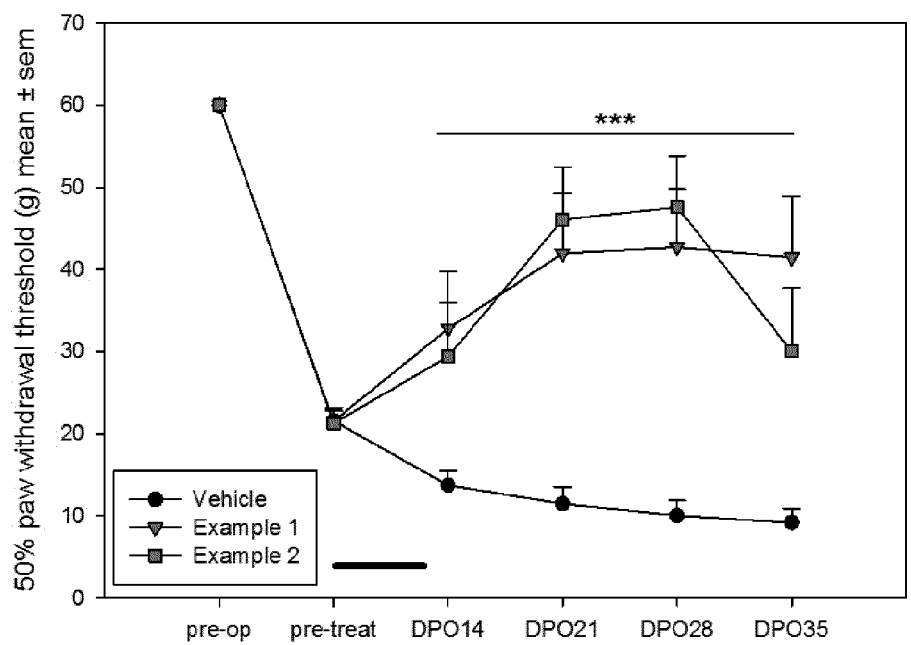
FIG. 1 (A) shows the 50% paw withdrawal threshold (g) after spinal nerve ligation (Chung model) and oral gavage of 10 mg/kg of Example 1 (2-Cyano-3-cyclopropyl-3-hydroxy-N-(3-methyl-4-trifluormethyl-phenyl)-thioacrylamide), Example 2 (2-Cyano-3-cyclopropyl-N-(4-fluoro-3-methyl-phenyl)-3-hydroxy-thioacrylamide) or vehicle from DPO7 (pre-treat) till DP012. *** p<0.001
Figure 1:
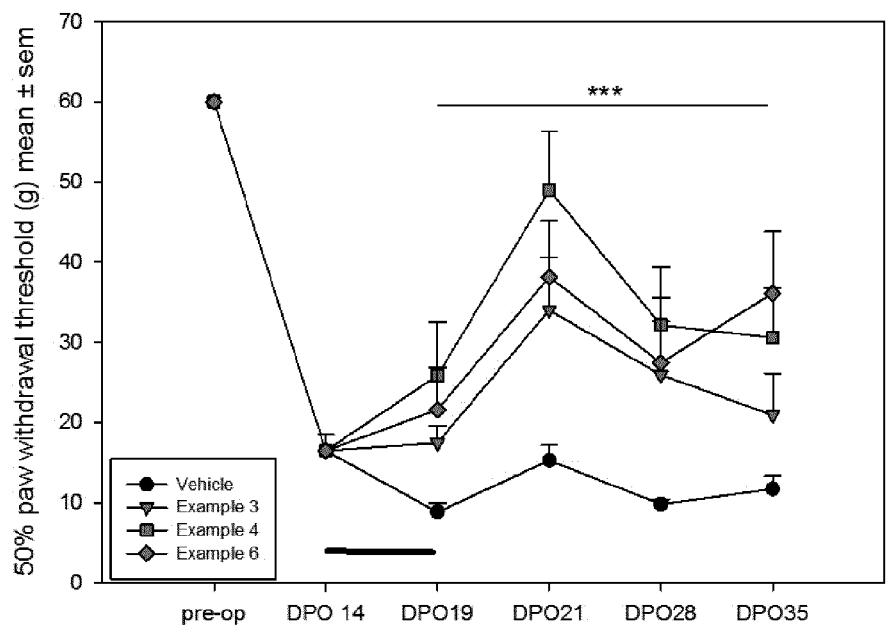

The embodiments of the disclosure described above are intended to be merely exemplary, and those skilled in the art will recognize, or will be able to ascertain using no more than routine experimentation, numerous equivalents of specific compounds, materials, and procedures. All such equivalents are considered to be within the scope of the disclosure.

DETAILED DESCRIPTION

The compounds of the present disclosure are useful in the treatment of diseases and disorders, which are responsive to modulation of the $GABA_A$ receptor complex. The $GABA_A$ receptor superfamily represents one of the classes of receptors through which the major inhibitory neurotransmitter, gamma -aminobutyric acid, or GABA, acts. Widely, although unequally, distributed through the mammalian brain, GABA mediates many of its actions through a complex of proteins called the $GABA_A$ receptor, which causes alteration in chloride conductance and membrane polarization.

A number of cDNAs for $GABA_A$ receptor subunits have been characterized. To date at least 6 alpha, 3 beta, 3 gamma, 1 epsilon, 1 delta and 2 rho subunits have been identified. It is generally accepted that native GABA A receptors are typically composed of 2 alpha, 2 beta, and 1 gamma subunits (Pritchett and Seeburg Science 1989; 245:1389-1392 and Knight et. al., Recept. Channels 1998; 6:1-18). Evidence such as message distribution, genome localization and biochemical study results suggest that the major naturally occurring receptor combinations are alpha 1 beta 2 gamma 2, alpha 2 beta 3 gamma 2, alpha 3 beta 3 gamma 2, and alpha 5 beta 3 gamma 2 (Mohler et. al. Neuroch. Res. 1995; 20(5): 631-636).

Disclosed are compounds, particularly compounds of formula I that bind to cell surface receptors. Preferred compounds of the invention bind to GABA receptors, in particular these compounds possess affinity for $GABA_A$ receptors. These compounds are therefore considered to be of potential use in the treatment of a broad array of diseases or disorders in patients which are characterized by modulation of $GABA_A$ receptors.

In a special embodiment, the compounds of the invention are considered useful for the treatment, prevention or alleviation of anxiety disorders, such as panic disorder with or without agoraphobia, agoraphobia without history of panic disorder, animal and other phobias including social phobias, obsessive-compulsive disorder, and generalized or substance-induced anxiety disorder; stress disorders including post-traumatic and acute stress disorder; sleep disorders; memory disorder; neuroses; convulsive disorders, for example epilepsy, or febrile convulsions in children; migraine, mood disorder; depressive or bipolar disorders, for example single episode or recurrent major depressive disorder, dysthymic disorder, bipolar I and bipolar II manic disorders, and cyclothymic disorder, psychotic disorders, including schizophrenia; neurodegeneration arising from cerebral ischemia; attention deficit hyperactivity disorder; pain and nociception; emesis, including acute, delayed and anticipatory emesis, in particular emesis induced by chemotherapy or radiation; motion sickness, post-operative nausea and vomiting; eating disorders including anorexia nervosa and bulimia nervosa; premenstrual syndrome; neuralgia, e.g. trigeminal neuralgia; muscle spasm or spasticity e.g. in paraplegic patients; the effects of substance abuse or dependency, including alcohol withdrawal; and cognitive disorders, such as Alzheimer's disease; cerebral ischemia, stroke, head trauma; tinnitus, disorders of circadian rhythm, e.g. in subjects suffering from the effects of jet lag or shift Work.

The novel compounds of the present disclosure are compounds of the formula I or a tautomeric isoform thereof

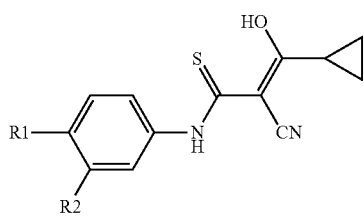

wherein R1 is selected from the group consisting of halogen, nitro, lower alkyl sulfonyl, cyano, trifluromethyl lower alkyl, lower alkoxy, lower alkoxycarbonyl, carboxy, lower alkyl aminosulfonyl, perfluoro lower alkyl, lower alkylthio, hydroxy lower alkyl, alkoxy lower alkyl, lower alkylthio lower alkyl, lower alkylsulfinyl lower alkyl, lower alkylsulfonyl lower alkyl, lower alkylsulfinyl, lower alkanoyl, aroyl, aryl, aryloxy, wherein the term "lower" as used above refers preferably to 1 to 3 carbon atoms, and R2 is selected from the group consisting of hydrogen, alkyl, alkoxy, alkylthio, and alkylcarbonyl, each alkyl residue having preferably 1 to 3 carbon atoms, and their tautomeric isoforms, non-toxic, pharmaceutically acceptable salts or pro-drugs thereof.

As used herein and unless otherwise indicated, the term "pharmaceutically acceptable salt" encompasses non-toxic acid and base addition salts of the compound to which the term refers. Acceptable non-toxic acid addition salts include those derived from organic and inorganic acids or bases know in the art, which include, for example, hydrochloric acid, hydrobromic acid, phosphoric acid, sulfuric acid, methanesulphonic acid, acetic acid, tartaric acid, lactic acid, succinic acid, citric acid, malic acid, maleic acid, sorbic acid, aconitic acid, salicylic acid, phthalic acid, embolic acid, enanthic acid, and the like. Compounds that are acidic in nature are capable of forming salts with various pharmaceutically acceptable bases. The bases that can be used to prepare pharmaceutically acceptable base addition salts of such acidic compounds are those that form non-toxic base addition salts, i.e., salts containing pharmacologically acceptable cations such as, but not limited to, alkali metal or alkaline earth metal salts and the calcium, magnesium, sodium or potassium salts in particular. Suitable organic bases include, but are not limited to, N,N-dibenzylethylenediamine, chloroprocaine, choline, diethanolamine, ethylenediamine, meglumaine (N-methylglucamine), lysine, arginine or histidine and procaine.

Physiologically acceptable salts of the 2-Cyano-3-cyclopropyl-3-hydroxy-N-aryl-thioacrylamide derivates according to the present disclosure can be metal or ammoniums salts of the substances/compounds according to the disclosure, which contain a free carboxylic group. Those which are particularly preferred are, for example, sodium, potassium, magnesium, or calcium, and also ammonium salts which are derived from ammonia, or organic amines, such as, for example, ethylamine, di- or tri-ethylamine, di- or triethanolamine, dimethylaminoethanol, arginine, lysine, histidine or ethylenediamine.

As used herein and unless otherwise indicated, the term "prodrug" means a derivative of a compound that can hydrolyze, oxidize, or otherwise react under biological conditions (in vitro or in vivo) to provide the compound. Examples of prodrugs include, but are not limited to, derivatives of compounds according to the present disclosure that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include derivatives of immunomodulatory compounds of the disclosure that comprise —NO, —NO2, —ONO, or —ONO2 moieties. Prodrugs can typically be prepared using well-known methods, such as those described in Burger's Medicinal Chemistry and Drug Discovery, 172-178, 949-982 (Manfred E. Wolff ed., 5th ed. 1995), and Design of Prodrugs (H. Bundgaard ed., Elsevier, New York 1985). As used herein and unless otherwise indicated, the terms "biohydrolyzable amide," "biohydrolyzable ester," "biohydrolyzable carbamate," "biohydrolyzable carbonate," "biohydrolyzable ureide," "biohydrolyzable phosphate" mean an amide, ester, carbamate, carbonate, ureide, or phosphate, respectively, of a compound that either: 1) does not interfere with the biological activity of the compound but can confer upon that compound advantageous properties in vivo, such as uptake, duration of action, or onset of action; or 2) is biologically inactive but is converted in vivo to the biologically active compound. Examples of biohydrolyzable esters include, but are not limited to, lower alkyl esters, lower acyloxyalkyl esters (such as acetoxylmethyl, acetoxyethyl, aminocarbonyloxymethyl, pivaloyloxymethyl, and pivaloyloxyethyl esters), lactonyl esters (such as phthalidyl and thiophthalidyl esters), lower alkoxyacyloxyalkyl esters (such as methoxycarbonyl-oxymethyl, ethoxycarbonyloxyethyl and isopropoxycarbonyloxyethyl esters), alkoxyalkyl esters, choline esters, and acylamino alkyl esters (such as acetamidomethyl esters). Examples of biohydrolyzable amides include, but are not limited to, lower alkyl amides, [alpha]-amino acid amides, alkoxyacyl amides, and alkylaminoalkylcarbonyl amides. Examples of biohydrolyzable carbamates include, but are not limited to, lower alkylamines, substituted ethylenediamines, amino acids, hydroxyalkylamines, heterocyclic and heteroaromatic amines, and polyether amines.

Examples of alkyl, alkoxy, alkylthio and alkylcarbonyl, each alkyl having of 1 to 3 carbon atoms, are methyl, ethyl, propyl, and isopropyl, methoxy ethoxy, propoxy and isopropoxy, methylthio, ethylthio, propylthio and isopropylthio and acetyl, ethylcarbonyl and propylcarbonyl. Halogen includes fluorine, chlorine, bromine and iodine.

Among the preferred compounds of formula I are those wherein R2 is hydrogen, methyl or ethyl and R1 is selected from the group consisting of fluorine, chlorine, jodine, trifluoromethyl, cyano, nitro, methansulfinyl, methansulfonyl, trifluoromethansulfinyl and trifluoronnethansulfonyl.

Especially preferred compounds are 2-cyano-3-cyclopropyl-3-hydroxy-N-(3-methyl-4-trifluormethyl-phenyl)-thioacrylamide, 2-cyano-3-cyclopropyl-3-hydroxy-N-(3-ethyl-4-trifluormethyl-phenyl)-thioacrylamide, 2-cyano-3-cyclopropyl-N-(4-fluoro-3-methyl-phenyl)-3-hydroxy-thioacrylamide, 2-cyano-3-cyclopropyl-N-(4-fluoro-3-ethyl-phenyl)-3-hydroxy-thioacrylamide, 2-cyano-3-cyclopropyl-N-(4-fluoro-phenyl)-3-hydroxy-thioacrylamide 2-cyano-3-cyclopropyl-3-hydroxy-N-(3-methyl-4-nitro-phenyl)-thioacrylamide, 2-cyano-3-cyclopropyl-3-hydroxy-N-(3-ethyl-4-nitro-phenyl)-thioacrylamide, 2-cyano-3-cyclopropyl-3-hydroxy-N-(4-nitro-phenyl)-thioacrylamide, 2-cyano-3-cyclopropyl-3-hydroxy-N-(4-trifluoromethane-sulfinyl-phenyl)-thioacrylamide, 2-cyano-N-(4-cyano-3-methyl-phenyl)-3-cyclopropyl-3-hydroxy-thioacrylamide, 2-cyano-N-(4-cyano-3-ethyl-phenyl)-3-cyclopropyl-3-hydroxy-thioacrylamide, 2-cyano-N-(4-cyano-phenyl-3-cyclopropyl-3-hydroxy-thioacrylamide, 2-cyano-3-cyclopropyl-3-hydroxy-N-(4-trifluoromethanesulfinyl-3-methyl-phenyl)-thioacrylamide, 2-cyano-3-cyclopropyl-3-hydroxy-N-(4-trifluoro-methanesulfonyl-phenyl)-thioacrylamide, 2-cyano-3-cyclopropyl-3-hydroxy-N-(4-trifluoromethane-sulfonyl-3-methyl-phenyl)-thioacrylamide, 2-cyano-3-cyclopropyl-3-hydroxy-N-(4-((trifluoromethyl)thio)phenyl)-thioacrylamide, 2-cyano-3-cyclopropyl-3-hydroxy-N-(3-methyl-4-((trifluoromethyl)thio)phenyl)-thioacrylamide, 2-cyano-3-cyclopropyl-N-(4-chloro-3-methyl-phenyl)-3-hydroxy-thioacrylamide, 2-cyano-3-cyclopropyl-N-(4-chloro-3-ethyl-phenyl)-3-hydroxy-thioacrylamide, 2-cyano-3-cyclopropyl-N-(4-chloro-phenyl)-3-hydroxy-thioacrylamide and their tautomeric isoforms, non-toxic, pharmaceutically acceptable salts or pro-drugs thereof.

The present disclosure does also relate to a pharmaceutical composition comprising a therapeutically effective amount of at least one of the compounds of formula I above or an tautomer thereof or any of its isomers or any mixture of its isomers, or a pharmaceutically acceptable salt thereof as defined above, optionally together with at least one acceptable and inert pharmaceutical carrier, excipient or diluent.

Furthermore, the present disclosure relates to the above compounds and compositions as a medicine, in particular for treatment, prevention or alleviation of anxiety disorders, such as panic disorder with or without agoraphobia, agoraphobia without history of panic disorder, animal and other phobias including social phobias, obsessive-compulsive disorder, and generalized or substance-induced anxiety disorder; stress disorders including post-traumatic and acute stress disorder; sleep disorders; memory disorder; neuroses; convulsive disorders, for example epilepsy, or febrile convulsions in children; migraine, mood disorder; depressive or bipolar disorders, for example single episode or recurrent major depressive disorder, dysthymic disorder, bipolar I and bipolar II manic disorders, and cyclothymic disorder, psychotic disorders, including schizophrenia; neurodegeneration arising from cerebral ischemia; attention deficit hyperactivity disorder; pain and nociception including chronic pain, acute pain, neuropathic pain, muscoskeletal pain, inflammatory pain, emesis, including acute, delayed and anticipatory emesis, in particular emesis induced by chemotherapy or radiation; motion sickness, post-operative nausea and vomiting; eating disorders including anorexia nervosa and bulimia nervosa; premenstrual syndrome; neuralgia, e.g. trigeminal neuralgia; muscle spasm or spasticity e.g. in paraplegic patients; the effects of substance abuse or dependency, including alcohol withdrawal; and cognitive disorders, such as Alzheimer's disease; cerebral ischemia, stroke, head trauma; tinnitus, disorders of circadian rhythm, e.g. in subjects suffering from the effects of jet lag or shift Work or of a living animal body, including a human, which disorder, disease or condition is responsive to modulation of the GABA$_A$ receptor complex. This can comprise the step of administering to such a living body in need thereof a therapeutically effective amount of a compound of composition as described above in detail.

Optically pure compositions can be asymmetrically synthesized or resolved using known resolving agents or chiral columns as well as other standard synthetic organic chemistry techniques. Compounds used in the disclosure may include compounds that are racemic, stereomerically enriched or stereomerically pure, and pharmaceutically acceptable salts, solvates, stereoisomers, and prod rugs thereof.

As used herein, and unless otherwise specified, the term "solvate" means a compound of the present disclosure or a salt thereof that further includes a stoichiometric or non-stoichiometric amount of solvent bound by non-covalent intermolecular forces. Where the solvent is water, the solvate is a hydrate.

As used herein, and unless otherwise specified, the term "stereoisomer" encompasses all enantiomerically/stereomerically pure and enantiomerically/stereomerically enriched compounds of this disclosure. Furthermore, the term "stereoisomer" includes also tautomers which are isomers of organic compounds that readily interconvert by a chemical reaction (tautomerization).

As used herein, and unless otherwise indicated, the term "stereomerically pure" or "enantiomerically pure" means that a compound comprises one stereoisomer and is substantially free of its counter stereoisomer or enantiomer. For example, a compound is stereomerically or enantiomerically pure when the compound contains 80%, 90%, or 95% or more of one stereoisomer and 20%, 10%, or 5% or less of the counter stereoisomer, in certain cases, a compound of the disclosure is considered optically active or stereomerically/enantiomerically pure {i.e., substantially the R-form or substantially the S-form) with respect to a chiral center when the compound is about 80% ee (enantiomeric excess) or greater, preferably, equal to or greater than 90% ee with respect to a particular chiral center, and more preferably 95% ee with respect to a particular chiral center.

As used herein, and unless otherwise indicated, the term "stereomerically enriched" or "enantiomerically enriched" encompasses racemic mixtures as well as other mixtures of stereoisomers of compounds of this disclosure {e.g., R/S=30/70, 35/65, 40/60, 45/55, 55/45, 60/40, 65/35 and 70/30). Various inhibitor compounds of the present disclosure contain one or more chiral centers, and can exist as racemic mixtures of enantiomers or mixtures of diastereomers. This disclosure encompasses the use of stereomerically pure forms of such compounds, as well as the use of mixtures of those forms. For example, mixtures comprising equal or unequal amounts of the enantiomers of a particular inhibitor compound of the disclosure may be used in methods and compositions of the disclosure. These isomers may be asymmetrically synthesized or resolved using standard techniques such as chiral columns or chiral resolving agents. See, e.g., Jacques, J., et al, Enantiomers, Racemates and Resolutions (Wiley-Interscience, New York, 1981); Wilen, S. H., et al, Tetrahedron 33:2725 (1977); Eliel, E. L., Stereochemistry of Carbon Compounds (McGraw-Hill, NY, 1962); and Wilen, S. H., Tables of Resolving Agents and Optical Resolutions p. 268 (E. L. Eliel, Ed., Univ. of Notre Dame Press, Notre Dame, Ind., 1972).

It should be noted that if there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

The term "physiologically functional derivative" as used herein refers to compounds which are not pharmaceutically active themselves but which are transformed into their pharmaceutical active form in vivo, i.e. in the subject to which the compound is administered. Examples of physiologically functional derivatives are prodrugs such as those described below in the present application.

The term "derivative" as used herein refers to a compound that is derived from a similar compound or a compound that can be imagined to arise from another compound, if one atom is replaced with another atom or group of atoms. The term "derivative" as used herein refers also to a compound that at least theoretically can be formed from the precursor compound (see Oxford Dictionary of Biochemistry and Molecular Biology. Oxford University Press. ISBN 0-19-850673-2.)

The suitability of a particular route of administration of an compound according to the present disclosure employed for a particular active agent will depend on the active agent itself (e.g., whether it can be administered orally without decomposing prior to entering the blood stream) and the disease being treated. An advantageous embodiment of the route of administration for a compound according to the present disclosure is orally. Further routes of administration are known to those of ordinary skill in the art.

The dosage of therapeutically effective amount of at least one compound varies from and also depends upon the age and condition of each individual patient to be treated. In an embodiment of the present disclosure, the recommended daily dose range of a compound according to the present disclosure for the conditions and disorders described herein lies within the range of from about, a daily dose of about 1 mg-10 g/body, preferable 5 mg-5 g/body and more preferable 10 mg-2 g/body of the active ingredient is generally given for preventing and /or treating this disease, and an average single dose of about 0.5-1 mg, 5 mg, 10 mg, 50 mg, 100 mg, 250 mg, 500 mg, 1 g, 2 g and 3 g is generally administered.

While the term for administering of at least one compound to prevent the diseases varies depending on species, and the nature and severity of the condition to be prevented, the compound may usually be administered to humans for a short term or a long term, i.e. for 1 week to 1 year.

Pharmaceutical compositions can be used in the preparation of individual, single unit dosage forms. The novel compounds of the present disclosure can be used in the form of pharmaceuticals compositions, for example, in solid, semisolid or liquid form, which contains one or more of the compounds according to the present disclosure as active ingredient associated with pharmaceutically acceptable carriers or excipient suitable for oral, parenteral such as intravenous, intramuscular, intrathecal, subcutaneous, enteral, intrarectal or intranasal administration. The active ingredient may be compounded, for example, with the usual non-toxic, pharmaceutically acceptable carriers for tablets, pellets, capsules, suppositories, solutions (saline for example), emulsion, suspensions (olive oil, for example), ointment and any other form suitable for use. The carriers which can be used are water, glucose, lactose gum acacia, gelatine, manitol, starch paste, magnesium trisilicate, corn starch, keratin, colloidal silica, potato starch, urea and other carriers suitable for use in manufacturing preparations, in solid, semisolid or liquid form, and in addition auxiliary, stabilizing, thickening and colouring agents and perfumes may be used. The active object compound is included in the pharmaceutical composition in an effective amount sufficient to prevent and/or treat the disease.

Single unit dosage forms of the disclosure are suitable for oral, mucosal (e.g., nasal, sublingual, vaginal, buccal, or rectal), parenteral (e.g., subcutaneous, intravenous, bolus injection, intramuscular, or intraarterial), topical (e.g., eye drops or other ophthalmic preparations), transdermal or transcutaneous administration to a patient. Examples of dosage forms include, but are not limited to: tablets; caplets; capsules, such as soft elastic gelatin capsules; cachets; troches; lozenges; dispersions; suppositories; powders; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; eye drops or other ophthalmic preparations suitable for topical administration; and sterile solids (e.g., crystalline or amorphous solids) that can be reconstituted to provide liquid dosage forms suitable for parenteral administration to a patient.

The composition, shape, and type of dosage forms of the disclosure will typically vary depending on their use. For example, a dosage form used in the acute treatment of a disease may contain larger amounts of one or more of the active agents it comprises than a dosage form used in the chronic treatment of the same disease. Similarly, a parenteral dosage form may contain smaller amounts of one or more of the active agents it comprises than an oral dosage form used to treat the same disease. These and other ways in which specific dosage forms encompassed by this disclosure will vary from one another will be readily apparent to those skilled in the art. See, e.g., Remington's Pharmaceutical Sciences, 18th ed., Mack Publishing, Easton Pa. (1990).

Typical pharmaceutical compositions and dosage forms comprise one or more excipients. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms. The suitability of a particular excipient may also depend on the specific active agents in the dosage form. For example, the decomposition of some active agents may be accelerated by some excipients such as lactose, or when exposed to water. Active agents that comprise primary or secondary amines are particularly susceptible to such accelerated decomposition. Consequently, this disclosure encompasses pharmaceutical compositions and dosage forms that contain little, if any, lactose or other mono- or di-saccharides. As used herein, the term "lactose-free" means that the amount of lactose present, if any, is insufficient to substantially increase the degradation rate of an active ingredient.

Lactose-free compositions of the disclosure can comprise excipients that are well known in the art and are listed, for example, in the U.S. Pharmacopeia (USP) 25-NF20 (2002). In general, lactose-free compositions comprise active ingredients, a binder/filler, and a lubricant in pharmaceutically compatible and pharmaceutically acceptable amounts. Preferred lactose-free dosage forms comprise active ingredients, microcrystalline cellulose, pre-gelatinized starch, and magnesium stearate.

This disclosure further encompasses anhydrous pharmaceutical compositions and dosage forms comprising active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, Drug Stability: Principles & Practice, 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms of the disclosure can be prepared using anhydrous or low moisture containing ingredients and low moisture or low humidity conditions. Pharmaceutical compositions and dosage forms that comprise lactose and at least one active ingredient that comprise a primary or secondary amine are preferably anhydrous if substantial contact with moisture and/or humidity during manufacturing, packaging, and/or storage is expected. An anhydrous pharmaceutical composition should be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g. vials), blister packs, and strip packs.

The disclosure further encompasses pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

Like the amounts and types of excipients, the amounts and specific types of active agents in a dosage form may differ depending on factors such as, but not limited to, the route by which it is to be administered to patients. However, typical dosage forms of the disclosure comprise a compound according to the present disclosure or a pharmaceutically acceptable salt, solvate, hydrate, stereoisomer, clathrate, or prodrug thereof in an amount of from about 0.10 to about 150 mg. Typical dosage forms comprise a compound according to the present disclosure or a pharmaceutically acceptable salt, solvate, hydrate, stereoisomer, clathrate, or prodrug thereof in an amount of about 0.1, 1, 2, 5, 7.5, 10, 12.5, 15, 17.5, 20, 25, 50, 100, 150 or 200 mg. In a particular embodiment, a preferred dosage form comprises a compound according to the present description in an amount of about 1, 2, 5, 10, 25 or 50 mg. In a specific embodiment, a preferred dosage form comprises a compound according to the present description in an amount of about 5, 10, 25 or 50 mg.

Oral Dosage Forms of pharmaceutical compositions of the disclosure that are suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, Remington's Pharmaceutical Sciences, 18th ed., Mack Publishing, Easton PA (1990).

Typical oral dosage forms of the disclosure are prepared by combining the active ingredients in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or non-aqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms of the disclosure include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives {e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, {e.g., Nos. 2208, 2906, 2910), microcrystalline cellulose, and mixtures thereof.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, Pa.), and mixtures thereof. A specific binder is a mixture of microcrystalline cellulose and sodium carboxymethyl cellulose sold as AVICEL RC-581. Suitable anhydrous or low moisture excipients or additives include AVICEL-PH-103(TM) and Starch 1500 LM. Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions of the disclosure is typically present in from about 50 to about 99 weight percent of the pharmaceutical composition or dosage form.

Disintegrants are used in the compositions of the disclosure to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms of the disclosure. The amount of disintegrant used varies based upon the type of formulation, and is readily discernible to those of ordinary skill in the art. Typical pharmaceutical compositions comprise from about 0.5 to about 15 weight percent of disintegrant, preferably from about 1 to about 5 weight percent of disintegrant.

Disintegrants that can be used in pharmaceutical compositions and dosage forms of the disclosure include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums, and mixtures thereof.

Lubricants that can be used in pharmaceutical compositions and dosage forms of the disclosure include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL200, manufactured by W.R. Grace Co. of Baltimore, Md.), a coagulated aerosol of synthetic silica (marketed by Degussa Co. of Piano, Tex.), CAB-O-SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

A preferred solid oral dosage form of the disclosure comprises a compound of the disclosure, anhydrous lactose, microcrystalline cellulose, polyvinylpyrrolidone, stearic acid, colloidal anhydrous silica, and gelatin.

Active ingredients of the disclosure can be administered by controlled release means or by delivery devices that are well known to those of ordinary skill in the art. Examples include, but are not limited to, those described in U.S. Pat. Nos.: 3,845,770; 3,916,899; 3,536,809; 3,598,123; and 4,008,719, 5,674,533, 5,059,595, 5,591,767, 5,120,548, 5,073,543, 5,639,476, 5,354,556, and 5,733,566, each of which is incorporated herein by reference. Such dosage forms can be used to provide slow or controlled-release of one or more active ingredients using, for example, hydroxypropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein can be readily selected for use with the active ingredients of the disclosure. The disclosure thus encompasses single unit dosage forms suitable for oral administration such as, but not limited to, tablets, capsules, gelcaps, and caplets that are adapted for controlled-release.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

Parenteral dosage forms can be administered to patients by various routes including, but not limited to, subcutaneous, intravenous (including bolus injection), intramuscular, and intra-arterial. Because their administration typically bypasses patients' natural defences against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions. Suitable vehicles that can be used to provide parenteral dosage forms of the disclosure are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyloleate, isopropyl myristate, and benzyl benzoate.

Compounds that increase the solubility of one or more of the active ingredients disclosed herein can also be incorporated into the parenteral dosage forms of the disclosure. For example, cyclodextrin and its derivatives can be used to increase the solubility of a compound of the disclosure and its derivatives. See, e.g., U.S. Pat. No. 5,134,127, which is incorporated herein by reference.

Topical and mucosal dosage forms of the disclosure include, but are not limited to, sprays, aerosols, solutions, emulsions, suspensions, eye drops or other ophthalmic preparations, or other forms known to one of skill in the art. See, e.g., Remington's Pharmaceutical Sciences, 16th and 18th eds., Mack Publishing, Easton Pa. (1980 & 1990); and Introduction to Pharmaceutical Dosage Forms, 4th ed., Lea & Febiger, Philadelphia (1985). Dosage forms suitable for treating mucosal tissues within the oral cavity can be formulated as mouthwashes or as oral gels.

Suitable excipients (e.g., carriers and diluents) and other materials that can be used to provide topical and mucosal dosage forms encompassed by this disclosure are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane-1,3-diol, isopropyl myristate, isopropyl palmitate, mineral oil, and mixtures thereof to form solutions, emulsions or gels, which are non-toxic and pharmaceutically acceptable. Moisturizers or humectants can also be added to pharmaceutical compositions and dosage forms if desired. Examples of such additional ingredients are well known in the art. See, e.g., Remington's Pharmaceutical Sciences, 16th and 18th eds., Mack Publishing, Easton Pa. (1980 & 1990).

The pH of a pharmaceutical composition or dosage form may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting composition.

Typically, active ingredients of the disclosure are preferably not administered to a patient at the same time or by the same route of administration. This disclosure therefore encompasses kits which, when used by the medical practitioner, can simplify the administration of appropriate amounts of active ingredients to a patient.

A typical kit of the disclosure comprises a dosage form of a compound of the disclosure, or a pharmaceutically acceptable salt, solvate, hydrate, stereoisomer, prodrug, or clathrate thereof. Kits encompassed by this disclosure can further comprise additional active agents. Examples of the additional active agents include, but are not limited to, those disclosed herein (see, e.g., section 4.2). Kits of the disclosure can further comprise devices that are used to administer the active ingredients. Examples of such devices include, but are not limited to, syringes, drip bags, patches, and inhalers.

The present invention relates furthermore to the use of the above compound of formula I or the above pharmaceutical composition for the treatment of diseases and disorders, which are responsive to modulation of GABA$_A$ receptor complex, in particular the following diseases: anxiety disorders, such as panic disorder with or without agoraphobia, agoraphobia without history of panic disorder, animal and other phobias including social phobias, obsessive-compulsive disorder, and generalized or substance-induced anxiety disorder; stress disorders including post-traumatic arid acute stress disorder; sleep disorders; memory disorder; neuroses; convulsive disorders, for example epilepsy, or febrile convulsions in children; migraine, mood disorder; depressive or bipolar disorders, for example single episode or recurrent major depressive disorder, dysthymic disorder, bipolar I and bipolar II manic disorders, and cyclothymic disorder, psychotic disorders, including schizophrenia; neurodegeneration arising from cerebral ischemia; attention deficit hyperactivity disorder; pain and nociception; emesis, including acute, delayed and anticipatory emesis, in particular emesis induced by chemotherapy or radiation; motion sickness, post-operative nausea and vomiting; eating disorders including anorexia nervosa and bulimia nervosa; premenstrual syndrome; neuralgia, e.g. trigeminal neuralgia; muscle spasm or spasticity e.g. in paraplegic patients; the effects of substance abuse or dependency, including alcohol withdrawal; and cognitive disorders, such as Alzheimer's disease; cerebral ischemia, stroke, head trauma; tinnitus, disorders of circadian rhythm, e.g. in subjects suffering from the effects of jet lag or shift Work. Furthermore, the present invention relates to a process for the preparation of the compounds of formula I comprising reacting a compound of the formula

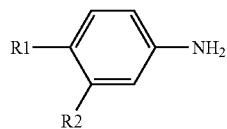

II wherein R1 and R2 have the above definitions with thiophosgen to a mixture of the respective amine (formula II) and sodium hydrogen carbonate in dichlormethane and water to form a compound of the formula

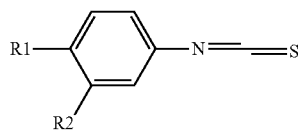

III and then successively reacting the latter with 3-cyclopropyl-3-oxo-propionitrile to obtain the compound of formula I. Preferably, the reaction of the compounds of formula III and 3-cyclopropyl-3-oxo-propionitrile is effected in the presence of potassium tert-butylate in an anhydrous organic solvent such as tetrahydrofuran or dichlormethane.

The general reaction for preparing the compound of formula I can be described by the following equations, wherein R1 and R2 have the above meanings.

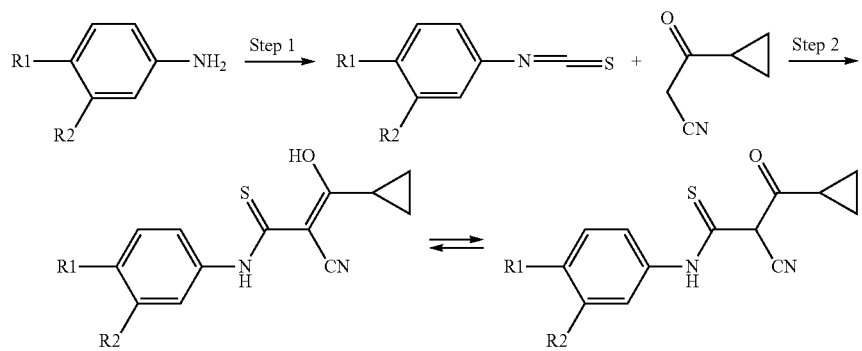

The general procedure for the manufacturing of the novel 2-cyano-3-cyclopropyl-3-hydroxy-N-aryl-thioacrylamide derivatives is as follows.

In a first step, thiophosgen can be added to a mixture of the respective amine of formula II and sodium hydrogen carbonate in an organic solvent, e.g. dichlormethane, and water at a temperature of for example about 5° C. The reaction medium can be stirred at ambient temperature (e.g. 20° C.) for e.g. 30 minutes. The phases can be separated and the water layer can be extracted with an organic solvent, which is not miscible with water, e.g. dichloromethane. The combined organic layers can be dried with e.g. Na₂SO₄ and concentrated for example under reduced pressure, for example not lower than 200 mbar, at 40° C. The obtained isothiocyanate is to be used for the second step.

In the second step, to a cooled solution of potassium tert-butylate in an organic solvent, e.g. THF, was added a solution of 3-cyclopropyl-3-oxo-propionitril in an organic solvent, e.g. THF over e.g. about 30 minutes, while maintaining cooling, e.g. a temperature of about 0° C. After reacting, e.g. stirring for a certain time, e.g. about 1 hour, at e.g. about 0° C., the solution was cooled to a temperature below about 0° C., e.g. about −20° C. The respective isothiocyanate was dissolved in an organic solvent, e.g. THF, and added to the solution, e.g. over about 25 minutes. The reaction was allowed to warm to ambient temperature. The completion of the reaction can be checked in usual ways, e.g. by TLC. Furthermore, the product can be purified and isolated in the usual way, e.g. by extraction, drying and recristallization.

The following examples illustrate the present invention without restricting it thereto.

EXAMPLES

General Procedure 1

Thiophosgen (114 mmol, 1.25 equiv.) was added dropwise to a mixture of the respective amine (91 mmol, 1 equiv.) and sodium hydrogen carbonate (318 mmol, 3.5 equiv.) in dichloromethane (240 ml) and water (240 ml) at 5° C. The reaction medium was vigorously stirred at ambient temperature for 30 min. The phases were separated and the water layer was extracted with dichloromethane (50 ml). The combined organic layers were dried with Na₂SO₄ and concentrated under vacuum (not lower than 200 mbar at 40° C.). The obtained isothiocyanate was used directly in the next step.

General Procedure 2

To a cooled solution of potassium tert-butylate (91.6 mmol, 1.1 equiv.) in THF (260 ml) was added a solution of 3-cyclopropyl-3-oxo-propionitrile (83.2 mmol, 1.0 equiv.) in THF (130 ml) over 30 minutes, while maintaining the temperature at 0° C. After stirring for an additional hour at 0° C., the solution was cooled to −20° C. The respective isothiocyanate (83.2 mmol, 1.0 equiv.) was dissolved in THF (130 ml) and added to the orange solution over 25 minutes. The reaction mixture was allowed to warm to room temperature. TLC indicated complete conversion of starting material. The clear solution was poured onto ice-cold 1N HCl (1 L), extracted with dichloromethane (1 L), dried over Na₂SO₄ and evaporated to dryness. The resulting raw-solid was recrystallized from MTBE.

Example 1

2-Cyano-3-cyclopropyl-3-hydroxy-N-(3-methyl-4-trifluormethyl-phenyl)-thioacrylamide 4-Isothiocyanato-2-methyl-1-trifluoromethyl-benzene was prepared according to General Procedure 1 using 15.9 g of 3-methyl-4-trifluoromethyl-phenylamine (prepared according to literature reference EP 1500643). The intermediate was obtained as orange oil in 100% yield (Step 1) and used in the next step without further purification. The product from step 1 (19.7 g) was reacted with 9.9 g of 3-cyclopropyl-3-oxo-propionitrile according to General Procedure 2.

Example 2

2-Cyano-3-cyclopropyl-N-(4-fluoro-3-methyl-phenyl)-3-hydroxy-thioacrylamide was prepared according to General Procedure 2 using 13 g of 4-fluoro-3-methylphenyl-isothiocyanate (purchased from Chempur).

Example 3

2-Cyano-3-cyclopropyl-3-hydroxy-N-(3-methyl-4-nitrophenyl)-thioacrylamide4-Isothiocyanato-2-methyl-1-nitrobenzene was prepared according to General Procedure 1 using 24 g of 3-methyl-4-nitroaniline (purchased from TCI). The intermediate was obtained as a pale brown solid in 99% yield and used in the next step without further purification. The product from step 1 (27.1 g) was reacted with 15.2 g of 3-cyclopropyl-3-oxo-propionitrile according to General Procedure 2.

Example 4

2-Cyano-3-cyclopropyl-3-hydroxy-N-(4-nitro-phenyl)-thioacrylamide

2-Cyano-3-cyclopropyl-3-hydroxy-N-(4-nitro-phenyl)-thioacrylamide was prepared according to General Procedure 2 using 15 g of 4-nitrophenyl isothiocyanate (purchased from Aldrich).

Example 5

2-Cyano-3-cyclopropyl-3-hydroxy-N-(4-trifluoromethylsulfanyl-phenyl)-thioacrylamide 1-Isothiocyanato-4-trifluoromethylsulfanyl-benzene was prepared according to General Procedure 1 using 15 g of 4-(trifluoromethylthio) aniline (purchased from Sinochem). The intermediate was obtained as orange-yellow needles in 99% yield and used in the next step without further purification. The product from step 1 (18.4 g) was reacted with 8.5 g of 3-cyclopropyl-3-oxo-propionitrile according to General Procedure 2.

Example 6

2-Cyano-N-(4-cyano-3-methyl-phenyl)-3-cyclopropyl-3-hydroxy-thioacrylamide

4-Isothiocyanato-2-methyl-benzonitrile was prepared according to General Procedure 1 using 15 g of 4-amino-2-methyl-benzonitrile (prepared according to literature reference EP 1500643). The intermediate was obtained as an orange solid in 96% yield and used in the next step without further purification. The product from step 1 (19.1 g) was reacted with 11.9 g of 3-cyclopropyl-3-oxo-propionitrile according to General Procedure 2.

Example 7

2-Cyano-N-(4-cyano-phenyl)-3-cyclopropyl-3-hydroxy-thioacrylamide

2-Cyano-N-(4-cyano-phenyl)-3-cyclopropyl-3-hydroxy-thioacrylannide was prepared according to General Procedure 2 using 15 g of 4-cyanophenyl isothiocyanate (purchased from Alfa).

Example 8

2-Cyano-3-cyclopropyl-3-hydroxy-N-(4-trifluoromethanesulfinyl-phenyl)-thioacrylamide 1-Isothiocyanato-4-trifluoromethanesulfinyl-benzene was prepared according to General Procedure 1 using 27.9 g of 4-trifluoromethanesulfinyl-phenylamin (prepared according to literature reference WO2006/20358). The intermediate was obtained as an orange solid in 75% yield and used in the next step without further purification. The product from step 1 (30.8 g, 80% pure) was reacted with 13.4 g of 3-cyclopropyl-3-oxo-propionitrile according to General Procedure 2. Purification was performed by crystallization from ethanol.

Example 9

2-Cyano-3-cycopropyl-3-hydroxy-N-(4-trifluoromethanesulfonyl-phenyl)-thioacrylamide
1-Isothiocyanato-4-trifluoromethanesulfonyl-benzene was prepared according to General Procedure 1 using 12.7 g of 4-trifluoromethanesulfonyl-phenylamin (prepared according to literature reference WO2006/20358). The intermediate was obtained as brown oil in 94% yield and used in the next step without further purification. The product from step 1 (14.1 g) was reacted with 5.8 g of 3-cyclopropyl-3-oxo-propionitrile according to General Procedure 2.

Data of the spectrometric analysis and yields of the Examples are given in the following Table I Experimental Method I
$GABA_A$ Receptor Binding Assay:
The affinity of the test compounds for the GABA gated Cl-channel ($GABA_A$ receptor complex) in the rat cerebral cortex was determined in a radioligand binding assay (Lewin et al,. 1989). Membrane homogenates of cerebral cortex are incubated for 120 min at 22° C. with 3 nM [35S]TBPS (-t-butylbicyclophoorothionate) in the presence and absence of the test compound.

Following incubation, the samples are filtered rapidly under vacuum through glass fiber filters and rinsed several times with ice-cold buffer using a 96-sample cell harvester. The filters are dried then counted for radioactivity in a scintilliation counter using a scintillation cocktail (Microscint 0, Packard). Each compound was tested at several concentrations to calculate the $IC_{50}$ values of the affinity to the $GABA_A$ receptor complex in cerebral cortex of rats.

Results
The $IC_{50}$ values of the test compounds were given in the following Table II

TABLE I

| Example | $^1$H NMR (CDCl3, 500 MHz) | 13C-NMR (DMSO-d6, 125 MHz): | Yield (%) |
|---|---|---|---|
| 1 | 16.15 (d, J = 1.8 Hz, 1H), 8.76 (s, 1H), 7.67 (d, J = 8.4 Hz, 1H), 7.44 (d, J = 8.4 Hz, 1H), 7.40 (s, 1H), 2.51 (d, J = 1.4 Hz, 3H), 2.29 (m, 1H), 1.36 (m, 2H), 1.21 (m, 2H) | 190.0 (m), 188.9 (m), 139.9 (m), 128.8 (m), 126.9 (m), 122.9, 118.0 (m), 86.8, 79.6 (m), 78.0 (m), 21.0 (m), 18.0 (m), 13.6 (m), 12.1 (m) | 46 |
| 2 | 16.19 (d, J = 1.8 Hz, 1H), 8.67 (s, 1H), 7.19 (m, 2H), 7.06 (t, J = 8.5 Hz, 1H), 2.30 (d, J = 1.9 Hz, 3H), 2.28 (m, 1H), 1.35 (m, 2H), 1.20 (m, 2H) | 190.0, 188.3, 161.4, 159.4, 132.0 (d, J = 3.4 Hz), 129.5 (d, J = 5.7 Hz), 126.2 (d, J = 18.8 Hz), 125.6 (d, J = 8.5 Hz), 117.6, 115.8 (d, J = 23.9 Hz), 86.3, 17.4, 14.7 (d, J = 3.3 Hz), 11.7 | 65 |
| 3 | 16.06 (d, J = 1.8 Hz, 1H), 8.86 (s, 1H), 8.04 (d, J = 8.8 Hz, 1H), 7.55 (dd, J = 8.8 Hz, 2.3 Hz, 1H), 7.48 (d, J = 2.0 Hz, 1H), 2.61 (s, 3H), 2.24 (m, 1H), 1.34 (m, 2H), 1.20 (m, 2H) | 191.2, 188.0, 147.3, 140.6, 135.5, 129.1, 126.1, 123.7, 117.3, 87.2, 20.9, 17.8, 12.4 | 55 |
| 4 | 16.05 (d, J = 1.8 Hz, 1H), 8.87 (s, 1H), 8.30 (m, 2H), 7.72 (m, 2H), 2.30 (m, 1H), 1.40 (m, 2H), 1.26 (m, 2H) | 191.4, 188.1, 146.2, 142.3, 125.9, 124.8, 117.3, 87.3, 17.9, 12.5 | 97 |
| 5 | ⬚16.15 (d, J = 1.8 Hz, 1H), 8.88 (s, 1H), 7.71 (m, 2H), 7.57 (m, 2H), 2.27 (m, 1H), 1.36 (m, 2H), 1.20 (m, 2H) | ⬚190.7, 187.9, 139.1, 137.0, 129.0 (q, J = 308.4 Hz), 126.6, 123.5, 117.4, 86.9, 17.6, 12.0 | 68 |
| 6 | 16.08 (d, J = 1.8 Hz, 1H), 8.80 (s, 1H), 7.65 (m, 1H), 7.48 (m, 1H), 7.46 (s, 1H), 2.58 (s, 3H), 2.27 (m, 1H),), 1.37 (m, 2H), 1.23 (m, 2H) | 190.9, 187.9, 143.4, 140.4, 133.3, 126.9, 123.4, 117.5, 117.3, 111.6, 86.9, 20.7, 17.7, 12.2 | 70 |
| 7 | ⬚16.03 (d, J = 1.8 Hz, 1H), 8.80 (s, 1H), 7.69 (m, 2H), 7.62 (m, 2H), 2.27 (m, 1H), 1.36 (m, 2H), 1.21 (m, 2H) | ⬚191.2, 188.0, 140.6, 133.2, 126.1, 118.2, 117.3, 111.2, 87.2, 17.8, 12.4 | 85 |
| 8 | 16.10 (d, J = 1.8 Hz, 1H), 8.94 (s, 1H), 7.86 (d, J = 8.6 Hz, 2H), 7.79 (m, 2H), 2.28 (m, 1H), 1.38 (m, 2H), 1.24 (m, 2H) | 191.1, 188.1, 141.5, 134.2, 126.9, 126.6, 125.0 (q, J = 335.2 Hz), 117.3, 87.0, 17.7, 12.3 | 42 |
| 9 | 16.04 (d, J = 1.8 Hz, 1H), 8.99 (s, 1H), 8.09 (d, J = 8.7 Hz, 2H), 7.91 (m, 2H), 2.29 (m, 1H), 1.41 (m, 2H), 1.26 (m, 2H) | 191.7, 188.2, 144.3, 131.9, 125.9, 120.0 (q, J = 325.8 Hz), 117.2, 87.5, 17.9, 12.6 | 56 |

Pharmacological Data and Activity

A series of non-clinical pharmacology studies have been performed to support the clinical evaluation of the compounds according to the present disclosure in human subjects. These studies were performed in accordance with internationally recognized guidelines for study design and in compliance with the requirements of Good Laboratory Practice (GLP) unless otherwise noted.

TABLE II

| Example | $IC_{50}$ values (μM) |
|---|---|
| 1 | 5.3 |
| 2 | 8.3 |
| 3 | 6.0 |
| 4 | 8.7 |
| 5 | 7.7 |

TABLE II-continued

| Example | IC$_{50}$ values (µM) |
|---|---|
| 6 | 7.9 |
| 7 | 9.6 |
| 8 | 10.3 |
| 9 | 5.0 |

Experimental Method II

Electrophysiological assays on different subunit combinations of the human GABA$_A$ receptor complex.

The functional positive modulation activity of the test compounds were investigated by using patch clamp techniques on HEK293 cells stably expressing different subunit combinations of the human GABA$_A$ receptor complex. In brief, the peak inward currents in response to the GABA (natural ligand of the GABA$_A$ receptors) additions in the presence of increasing concentrations of test compound were measured. To calculate the positive modulation activity the mean effect of GABA (EC20 concentration) was set to 100%. In addition, all measured currents of the test compounds have been normalized (in percent) to the current elicited by the addition of the EC20 concentration of the natural ligand GABA.

Results:

Table III shows the normalized percent current values for each test compound assayed on the different human GABA$_A$ receptor subunit combinations. A value of 100 percent equates to the compound having an effect equivalent to the addition of the EC20 concentration of GABA.

TABLE III

| Test compound | Concentration (µM) | GABA$_A$ α3β3γ2 (%) | GABA$_A$ α2β3γ2 (%) | GABA$_A$ α1β3γ2 (%) |
|---|---|---|---|---|
| Example 1 | 10 | 697 | 614 | 792 |
| Example 2 | 50 | 835 | 470 | 734 |
| Example 3 | 50 | 469 | 380 | 424 |
| Example 4 | tba | tba | tba | tba |
| Example 5 | 10 | 315 | 453 | 707 |
| Example 6 | 10 | 357 | 286 | 338 |
| Example 7 | tba | tba | tba | tba |
| Example 8 | tba | tba | tba | tba |
| Example 9 | 10 | 328 | 259 | 286 |

Experimental Method III

Treatment with the compounds of either Example 1, Example 2, Example 3, Example 4 or Example 6 can reverse neuropathic pain induced by spinal nerve ligation (SNL) injury in the rat.

Description of the Method

SNL model or Chung model as in vivo model for peripheral neuropathic pain

Surgery was performed according to the method of Chung et al., 2004 (see List of References). In brief, animals are anesthetized and the hair on their backs is trimmed. Under sterile conditions, a longitudinal incision is made at the lower lumbar and sacral levels, exposing the paraspinal muscles on the left. Connective tissues and muscles are removed by a small scraper, after which bony structures become visible. The L6 vertebra left transverse process of animal was first removed to expose the L4 and L5 spinal nerves. The L5 spinal nerve was then carefully isolated and tightly ligated with 6-0 silk thread. Surgery was always performed on the left leg (Ipsilateral paw), the right leg (contralateral paw) remained intact and served as a control. On completion of the operation, hemostasis is confirmed and the muscles are sutured in layers using silk thread and the skin is closed with metal clips, anesthesia is then discontinued. Axonal degeneration occurs, with all types of axons being approximately equally affected. Pronounced mechanical allodynia follows, accompanied by spontaneous pain behaviors, which lasts for several weeks without recovery. Mechanical allodynia is typically assessed beginning 1-2 weeks post-surgery.

Assessment of Mechanical Allodynia

Mechanical allodynia thresholds were determined according to the methods described by Chaplan and colleagues (Chaplan et al., 1994). At the designated post-operative time points the injured rats were placed in an elevated clear-plastic, wire mesh-bottomed cage. After a 10- to 15-min acclimation period, eight von Frey filaments (Stoelting, Wood Dale, Ill.) with bending forces ranging from 2 to 60 g were used to determine the 50% mechanical threshold for paw withdrawal using the up-and-down method.

Experiment 1 in the Chung Model (FIG. 1a)

After spinal nerve ligation (SNL) injury, individual rats were randomly assigned into a treatment group. The following groups were used:

Group 1: SNL+ only vehicle (Carboxymethylcellulose and sterile water) by oral gavage for 5 days from DPO7 (pre-treat) till DPO12.

Group 2: SNL+ Example 1 (10 mg/kg) in vehicle by oral gavage for 5 days from DPO7 (pre-treat) till DPO12.

Group 3: SNL+ Example 2 (10 mg/kg) in vehicle by oral gavage for 5 days from DPO7 (pre-treat) till DPO12.

Results

The nociceptive threshold is defined as the force (g) at which the rat withdraw its paw (cut-off force 60 g). Before injury the threshold was 60 g for the ipsilateral paw in all animals. As consequence of the spinal nerve ligation the nociceptive threshold decreased to about 20 g in all groups one week after injury as shown in FIG. 1a. At this time point (pre-treat or DPO7) the 5 day oral treatment with Example 1, Example 2 or vehicle started. The withdrawal threshold in the vehicle treated animals remained stable at 10 g in the following weeks. As a consequence of the Example 1 treatment the threshold increased to about 45 to 50 g (DPO21 and DPO28) and remained at 30 g (DPO35) till the end of the experiment. As shown in FIG. 1a the withdrawal threshold of rats treated with Example 2 increased to 40 g at DPO21 and remained there till the end of the experiment on DP035. Statistical testing revealed a very strong significant difference between the two treatment groups and the vehicle control group from DP014 till DP035 (Two-way ANOVA, RM, p<0,001) (FIG. 1a). Thus, Example 1 (2-Cyano-3-cyclopropyl-3-hydroxy-N-(3-methyl-4-trifluormethyl-phenyl)-thioacrylamide) and Example 2 (2-Cyano-3-cyclopropyl-N-(4-fluoro-3-methyl-phenyl)-3-hydroxy-thioacrylamide) can both reverse neuropathic pain induced by spinal nerve ligation.

Experiment 2 in the Chung Model (FIG. 1b)

After spinal nerve ligation (SNL) injury, individual rats were randomly assigned into a treatment group. The following groups were used:

Group 1: SNL+ only vehicle (Carboxymethylcellulose and sterile water) by oral gavage for 5 days from DPO14 till DPO19.

Group 2: SNL+ Example 3 (10 mg/kg) in vehicle by oral gavage for 5 days from DPO14 till DPO19.

Group 3: SNL+ Example 4 (10 mg/kg) in vehicle by oral gavage for 5 days from DPO14 till DPO19.

Group 4: SNL+ Example 6 (10 mg/kg) in vehicle by oral gavage for 5 days from DPO14 till DPO19.

Results

The nociceptive threshold is defined as the force (g) at which the rat withdraw its paw (cut-off force 60 g). Before injury the threshold was 60 g for the ipsilateral paw in all animals. As consequence of the spinal nerve ligation the nociceptive threshold decreased to about 18 g in all groups one week after injury (DPO14). At this time point (DPO14) the 5 day oral treatment with Example 3, Example 4, Example 6 or vehicle started. The withdrawal threshold in the vehicle treated animals remained stable at 10 to 20 g in the following weeks. As a consequence of the Example 3 treatment the threshold increased to about 35 g at DPO21 and remained at nearly 23-25 g till the end of the experiment at DPO35. The withdrawal threshold of rats treated with Example 4 increased to nearly 50 g at DPO21 and remained at 30 g till the end of the experiment on DPO35. As also shown in FIG. 1b the withdrawal threshold of rats treated with Example 6 increased to nearly 40 g at DPO21 and remained at nearly 28 to 38 g till the end of the experiment on DPO35. Statistical testing revealed a very strong significant difference between the three treatment groups and the vehicle control group from DPO19 till DP035 (Two-way ANOVA, RM, $p<0,001$) (FIG. 1b). Thus, Example 3 (2-Cyano-3-cyclopropyl-N-(4-fluoro-3-methyl-phenyl)-3-hydroxy-thioacrylamide), Example 40 and Example 6 (2-Cyano-N-(4-cyano-3-methyl-phenyl)-cyclopropyl-3-hydroxy-thioacrylamide) can both reverse neuropathic pain induced by spinal nerve ligation.

Experimental Method V

Treatment with either Example 1, Example 2, Example 3 or Example 6 can reverse acute pain induced by capsaicin injection in the hindpaw of the rat.

Description of the Method

Capsaicin induced pain as in vivo model for acute pain

Rats were gently restrained and capsaicin (10 μg in 10 μl of 10% Tween80) in saline was injected into the plantar surface of the hindpaw using a 0.3 ml insulin syringe with a 29-gauge needle (Terumo Europe, Belgium).

Figure 2:
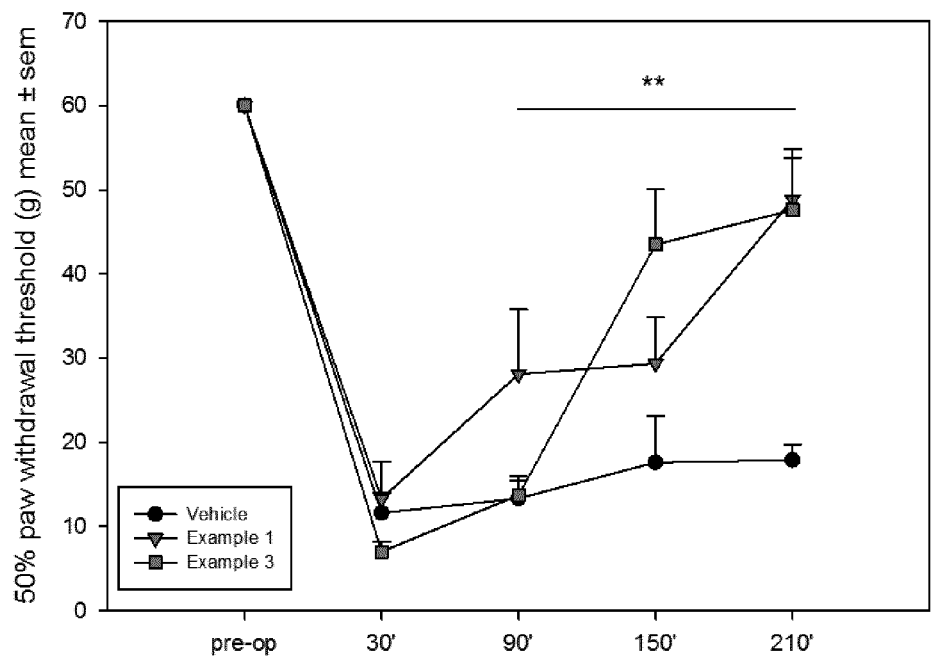
FIG. 2 (A) shows the 50% paw withdrawal threshold (g) after capsaicin induced pain and oral gavage of 1 mg/kg of Example 1 (2-Cyano-3-cyclopropyl-3-hydroxy-N-(3-methyl-4-trifluormethyl-phenyl)-thioacrylamide), Example 3 (2-Cyano-3-cyclopropyl-3-hydroxy-N-(3-methyl-4-nitro-phenyl)-thioacrylamide) or vehicle about 40 minutes after capsaicin injection. ** p<0.01
Figure 2:
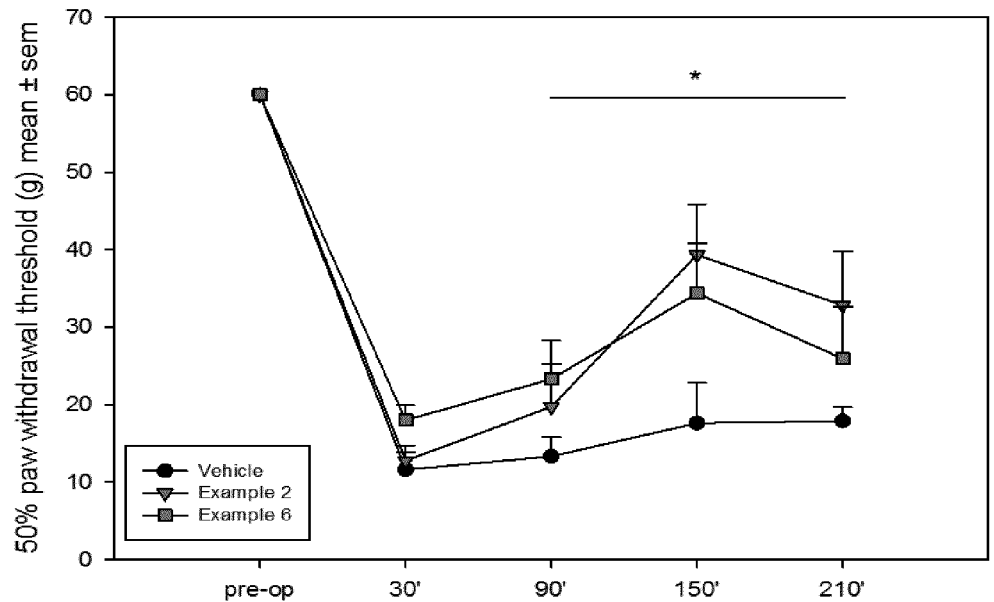

Experiment 1 in the Capsaicin Model (FIG. 2a)

After injection of Capsaicin, individual rats were randomly assigned into a treatment group. The following groups were used:

Group 1: Capsaicin injection+ only vehicle (Carboxymethylcellulose and sterile water) by oral gavage about 40 minutes after injection.

Group 2: Capsaicin injection+ Example 1 (1 mg/kg) in vehicle by oral gavage about 40 minutes after injection.

Group 3: Capsaicin injection+ Example 3 (1 mg/kg) in vehicle by oral gavage about 40 minutes after injection.

Assessment of Mechanical Allodynia

For the assessment of mechanical allodynia see experimental method 111/description of the method.

Results

The nociceptive threshold is defined as the force (g) at which the rat withdraw its paw (cut-off force 60 g). Before capsaicin injection the threshold was 60 g for the ipsilateral paw in all animals. Thirty minutes after the injection the nociceptive threshold was assessed again and decreased to about 7-14 g in all groups. The assessment was directly followed by the administration of Example 1, Example 3 or vehicle. As shown in FIG. 2a the withdrawal threshold of rats treated with Example 1 increased rapidly to 30 g after 150 minutes and reached nearly 50 g at 210 minutes after capsaicin injection. As a consequence of the Example 3 treatment the withdrawal threshold increased slowly and reached 40 g after 150 minutes and nearly 50 g at 210 minutes after capsaicin injection. The vehicle treated animals on the contrary remained at a withdrawal threshold between 10-20 g (FIG. 2a). Statistical testing revealed a strong significant difference between the two treatment groups and vehicle (Two-way ANOVA RM; $p<0.01$). Thus, Example 1 (2-Cyano-3-cyclopropyl-3-hydroxy-N-(3-methyl-4-trifluormethyl-phenyl)-thioacrylamide) and Example 3 (2-Cyano-3-cyclopropyl-3-hydroxy-N-(3-methyl-4-nitro-phenyl)-thioacrylannide) can both reverse acute mechanical allodynia induced by capsaicin.

Experiment 2 in the Capsaicin Model (FIG. 2b)

After injection of Capsaicin, individual rats were randomly assigned into a treatment group. The following groups were used:

Group 1: Capsaicin injection+ only vehicle (Carboxymethylcellulose and sterile water) by oral gavage about 40 minutes after injection.

Group 2: Capsaicin injection+ Example 2 (10 mg/kg) in vehicle by oral gavage about 40 minutes after injection.

Group 3: Capsaicin injection+ Example 6 (10 mg/kg) in vehicle by oral gavage about 40 minutes after injection.

Assessment of Mechanical Allodynia

For the assessment of mechanical allodynia see experimental method 111/description of the method.

Results

The nociceptive threshold is defined as the force (g) at which the rat withdraw its paw (cut-off force 60 g). Before capsaicin injection the threshold was 60 g for the ipsilateral paw in all animals. Thirty minutes after the injection the nociceptive threshold was assessed again and decreased to about 10-17 g in all groups. The assessment was directly followed by the administration of Example 2, Example 6 or vehicle. As shown in FIG. 2b the withdrawal threshold of rats treated with Example 2 increased rapidly to nearly 40 g after 150 minutes and remained at nearly 33 g at 210 minutes after capsaicin injection. As a consequence of the Example 6 treatment the withdrawal threshold increased slowly and reached 35 g after 150 minutes and remained at 25 g at 210 minutes after capsaicin injection. The vehicle treated animals on the contrary remained at a withdrawal threshold between 10-20 g (FIG. 2b). Statistical testing revealed a significant difference between the two treatment groups and vehicle (Two-way ANOVA RM; $p<0.05$). Thus, Example 2 (2-Cyano-3-cyclopropyl-N-(4-fluoro-3-methyl-phenyl)-3-hydroxy-thioacrylamide) and Example 6 (2-Cyano-N-(4-cyano-3-methyl-phenyl)-3-cyclopropyl-3-hydroxy-thio-acrylarnide) can both reverse acute mechanical allodynia induced by capsaicin.

The embodiments of the disclosure described above are intended to be merely exemplary, and those skilled in the art will recognize, or will be able to ascertain using no more than routine experimentation, numerous equivalents of specific compounds, materials, and procedures. All such equivalents are considered to be within the scope of the disclosure.

List of References

The following additional publications are incorporated herein by references:

WO 00/69842 A1
EP 731 099 A1
US 2003/0229134
EP 1500643
WO2006/20358
Chaplan, S. R., et al., 1994. Quantitative assessment of tactile allodynia in the rat paw. J Neurosci Methods. 53, 55-63.

Chung, J. M., et al., 2004. Segmental Spinal Nerve Ligation Model of Neuropathic Pain. Methods in Molecular Medicine, Vol. 99: Pain Research: Methods and Protocols Lewin, A. H., De Costa, B. R., Rice, K. C. and Skolnick, P. (1989). Meta- and para-isothiocyanato-t-butylbicycloorthobenzoate: irreversible ligands of the aminobutyric acid-regulated chloride ionophore. Mol. Pharmacol., 35:189.

What is claimed is:

1. A compound of the formula I or a tautomeric isoform thereof

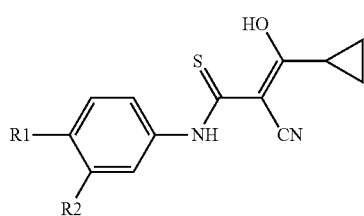
(I)

wherein R1 is selected from the group consisting of a halogen, a nitro, a cyano, and a trifluoromethyl lower alkyl, wherein the term "lower" is 1 to 3 carbon atoms; and wherein R2 is methyl, or a pharmaceutically acceptable base addition salt thereof.

2. The compound according to claim 1, wherein R1 is selected from the group consisting of fluorine, a trifluoromethyl, a cyano, and a nitro.

3. The compound according to claim 1, wherein the compound is selected from the group consisting of 2-cyano-3-cyclopropyl-3-hydroxy-N-(3-methyl-4-trifluoromethyl-phenyl)-thioacrylamide, 2-cyano-3-cyclopropyl-3-hydroxy-N-(3-methyl-4-nitro-phenyl)-thioacrylamide, 2-cyano-3-cyclopropyl-N-(4-fluoro-3-methyl-phenyl)-3-hydroxy-thioacrylamide, 2-cyano-N-(4-cyano-3-methyl-phenyl)-3-cyclopropyl-3-hydroxy-thioacrylamide, and their tautomeric isoforms, pharmaceutically acceptable salts thereof.

4. A pharmaceutical composition comprising a therapeutically effective amount of at least one compound according to claim 1, or a tautomer thereof, or a pharmaceutically acceptable salt thereof, optionally together with at least one acceptable and inert pharmaceutical carrier, excipient, or diluent.

5. The compound according to claim 1 embodied as a medicine.

6. The compound according to claim 1, wherein the compound is bound to a $GABA_A$ receptor complex and wherein the compound acts as a positive allosteric modulator of the GABAA receptor complex.

7. The compound according to claim 1, wherein the compound is 2-cyano-3-cyclopropyl-3-hydroxy-N-(3-methyl-4-nitro-phenyl)-thioacrylamide.

8. The compound according to claim 1, wherein the compound is selected from 2-cyano-3-cyclopropyl-3-hydroxy-N-(3-methyl-4-trifluoromethyl-phenyl)-thioacrylamide, 2-cyano-3-cyclopropyl-N-(4-fluoro-3-methyl-phenyl)-3-hydroxy-thioacrylamide, 2-cyano-N-(4-cyano-3-methyl-phenyl)-3-cyclopropyl-3-hydroxy-thioacrylamide, and 2-cyano-3-cyclopropyl-3-hydroxy-N-(3-methyl-4-nitro-phenyl)-thioacrylamide.

9. A method of treating a disorder responsive to modulation of the $GABA_A$ receptor complex in a subject having the disorder, the method comprising admitering to the subject a therapeutically effective amount of a compound according to claim 1, wherein the disorder is acute pain, chronic pain, or neuropathic pain.

10. The method according to claim 9, wherein the subject is a human.

11. The method according to claim 9, wherein R1 is selected from the group consisting of fluorine, a trifluoromethyl, a cyano, and a nitro.

12. The method according to claim 9, wherein the compound is selected from the group consisting of 2-cyano-3-cyclopropyl-3-hydroxy-N-(3-methyl-4-trifluoromethyl-phenyl)-thioacrylamide, 2-cyano-3-cyclopropyl-3-hydroxy-N-(3-methyl-4-nitro-phenyl)-thioacrylamide, 2-cyano-3-cyclopropyl-N-(4-fluoro-3-methyl-phenyl)-3-hydroxy-thioacrylamide, and 2-cyano-N-(4-cyano-3-methyl-phenyl)-3-cyclopropyl-3-hydroxy-thioacrylamide.

13. The compound according to claim 1, wherein the compound is

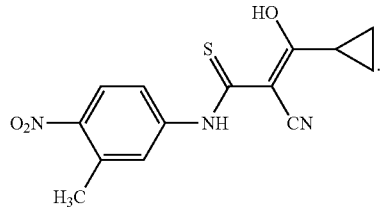 [SMILES: Cc1cc(NC(=S)/C(C#N)=C(\O)C2CC2)ccc1[N+](=O)[O-]]

* * * * *